United States Patent [19]

Fukuhara et al.

[11] Patent Number: 4,923,837

[45] Date of Patent: May 8, 1990

[54] HYDROGENATION CATALYST

[75] Inventors: Hiroshi Fukuhara; Fujihisa Matsunaga; Yasushi Nakashima, all of Ichihara, Japan

[73] Assignee: Mitsui Petrochemical Industries, Ltd., Tokyo, Japan

[21] Appl. No.: 286,024

[22] Filed: Dec. 19, 1988

[30] Foreign Application Priority Data

Dec. 29, 1987 [JP] Japan ................. 62-332527

[51] Int. Cl.$^5$ ................. B01J 21/00; B01J 21/16
[52] U.S. Cl. ................. 502/84
[58] Field of Search ................. 502/84

[56] References Cited

U.S. PATENT DOCUMENTS

| | | | |
|---|---|---|---|
| 3,767,720 | 10/1973 | Drinkard . | |
| 3,963,789 | 6/1976 | Kruse et al. | 502/84 |
| 4,197,415 | 4/1980 | Hideyuki et al. . | |
| 4,337,177 | 6/1982 | Drake | 502/84 |
| 4,495,373 | 1/1985 | Niwa et al. | 585/269 |
| 4,665,274 | 5/1987 | Ichihashi et al. . | |
| 4,774,212 | 9/1988 | Drezdon | 502/84 |

FOREIGN PATENT DOCUMENTS

| | | |
|---|---|---|
| 0190352 | 8/1986 | European Pat. Off. . |
| 0214530 | 3/1987 | European Pat. Off. . |
| 2294154 | 7/1976 | France . |
| 52-3933 | 1/1977 | Japan . |
| 57-130926 | 8/1982 | Japan . |
| 59-184138 | 10/1984 | Japan . |
| 62-45544 | 2/1987 | Japan . |

OTHER PUBLICATIONS

*Inorganic Chemistry*, vol. 26, No. 1, Jan. 1987, pp. 203-205, Giannelis et al, "Anionic Photocatalysts Supported in Layered Double . . . ".

*Primary Examiner*—Carl F. Dees
*Attorney, Agent, or Firm*—Nixon & Vanderhye

[57] ABSTRACT

A hydrogenation catalyst which is prepared by adsorbing ruthenium ions on a hydrotalcite (i.e. an anionic clay mineral) and/or a compound capable of conversion to a hydrotalcite structure by hydration, and then reducing said adsorbed ruthenium ions. The catalyst suitable for use in a process by which a monocyclic aromatic hydrocarbon is partially reduced to produce cyclohexene.

7 Claims, No Drawings

HYDROGENATION CATALYST

BACKGROUND OF THE INVENTION

The present invention relates to a hydrogenation catalyst. More particularly, the present invention relates to a catalyst suitable for use in a process by which a monocyclic aromatic hydrocarbon is partially reduced to produce a corresponding cycloolefin, in particular, cyclohexene in high selectivity and yield.

Cycloolefins are produced by partial hydrogenation, which is one kind of hydrogenation reaction, of aromatic hydrocarbon compounds. As is well known, it is difficult to obtain cycloolefins in high yield because the resulting cycloolefins are normally more reactive than the starting aromatic hydrocarbon compounds. If cycloolefins can be obtained in high yield by partial hydrogenation of aromatic hydrocarbon compounds, the reaction process can be simplified, which is preferred from an industrial viewpoint.

Various hydrogenation catalysts are employed in the process for producing cycloolefins by partial hydrogenation of aromatic hydrocarbon compounds, and the followings are typical examples:

(1) a catalyst composition containing water, an alkali agent and an element of group VIII in the periodic table (Japanese Patent Publication No. 56-22850);

(2) a ruthenium catalyst containing copper, silver, cobalt or potassium which is to be used together with water and a phosphate compound (Japanese Patent Publication No. 56-4536);

(3) a catalyst having chiefly ruthenium supported on a metal oxide such as silica or alumina and which is to be used in a process of performing partial hydrogenation in the presence of water and cobalt sulfate (Japanese Patent Public Disclosure No. 57-130926);

(4) a ruthenium catalyst supported on an oxide of nickel, cobalt, chromium, titanium or zirconium which is to be used in a process employing an alcohol or ester as an additive (Japanese Patent Publication No. 52-3933);

(5) a ruthenium-silica catalyst for use in a process of performing partial hydrogenation in the presence of water which is prepared by hydrolyzing a mixed solution of ruthenium glycoxide and ethyl silicate, then reducing the hydrolyzate with hydrogen at 400° C. (Japanese Patent Public Disclosure No. 59-155328);

(6) a ruthenium catalyst for use in a process of performing reaction with at least one of zinc oxide and zinc hydroxide being added as an activating component to the reaction system (Japanese Patent Public Disclosure No. 59-184138);

(7) a catalyst prepared by reducing Zn-containing ruthenium which is to be used in a process of performing partial hydrogenation in the presence of a water-soluble zinc compound (Japanese Patent Public Disclosure No. 62-45544); and (8) a catalyst having a ruthenium-based mixture of metallic elements supported on barium sulfate which is to be used in a process of performing reaction in the presence of one compound selected from among silicon dioxide, titanium dioxide and aluminum oxide (Japanese Patent Public Disclosure No. 62-61935).

However, if hydrogenation is performed using the known catalysts listed above, the conversion of the starting material must be held low in order to enhance the selectivity for the desired cyclohexenes, or the reaction rate is very low. Because of these and other reasons, the yield and production rate of cyclohexenes are generally low in the conventional processes. Furthermore, these processes are not necessarily best suited for commercial production of cyclohexenes because the use of large amounts of additives causes various problems such as increased complexity of the reaction system and the need to employ a corrosion-resistant reactor.

Under these circumstances, there has been a strong need for the development of a hydrogenation catalyst that allows the intended product to be obtained in high selectivity and yield.

SUMMARY OF THE INVENTION

An object, therefore, of the present invention is to eliminate the aforementioned defects of the prior art and to provide a novel hydrogenation catalyst which is typically suitable for use in the production of cycloolefins in an industrially advantageous way.

The present inventors conducted intensive studies in order to develop a hydrogenation catalyst that can be used in partial reduction of monocyclic aromatic hydrocarbons to produce corresponding cyclohexenes in improved selectivity and yield. The present invention has been accomplished as a result of these efforts.

The present invention provides a hydrogenation catalyst which is prepared by adsorbing ruthenium ions on a hydrotalcite (i.e., an anionic clay mineral) and/or a compound capable of conversion to a hydrotalcite structure by hydration, and then reducing said adsorbed ruthenium ions.

DETAILED DESCRIPTION OF THE INVENTION

Any material can be used as a support for the catalyst of the present invention and the only requirement is that it be a hydrotalcite or a compound that can be converted to a hydrotalcite structure by hydration. The hydrotalcite may be a synthetic hydrotalcite, a natural hydrotalcite or a mixture of both. Preferably, the support material is selected from among hydrotalcites of formula (1) noted below and compounds having the structure shown by formula (2) below which are solid solutions of oxides that are obtained by calcining said hydrotalcites and which can be converted to a hydrotalcite structure by hydation:

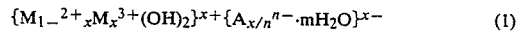
$$\{M_{1-x}^{2+}M_x^{3+}(OH)_2\}^{x+}\{A_{x/n}^{n-}\cdot mH_2O\}^{x-} \quad (1)$$

$$\{M_{1-x}^{2+}M_x^{3+}O_{1+x/2}\} \quad (2)$$

where $M^{2+}$ is a divalent metal such as $Mg^{2+}$, $Mn^{2+}$, $Fe^{2+}$, $Co^{2+}$, $Ni^{2+}$, $Cu^{2+}$ or $Zn^{2+}$ or a mixture of these metals; $M^{3+}$ is a trivalent metal such as $Al^{3+}$, $Fe^{3+}$, $Cr^{3+}$, $Co^{3+}$ or $In^{3+}$ or a mixture of these metals; $A^{n-}$ is an n-valent anion such as $OH^-$, $F^-$, $Cl^-$, $Br^-$, $NO_3^-$, $CO_3^{2-}$, $SO_4^{2-}$, $CH_3COO^-$, oxalate ion or salicylate ion, or a mixture of these ions; and $0 < X \leq 0.33$.

Hydrotalcites of formula (1) and compounds of formula (2) may be used either on their own or as admixtures.

Ruthenium ions to be adsorbed or supported on hydrotalcites may be of any type that originates from ruthenium compounds or metallic ruthenium. Useful ruthenium compounds include, for example, salts such as chloride, bromide, nitrate and sulfate, and complexes such as acetylacetonato complex salts and ammine complex salts. Trivalent or tetravalent ruthenium compounds are particularly preferred because of the ease of their availability and handling.

The amount of ruthenium ions to be adsorbed or supported on hydrotalcites in accordance with the present invention is adjusted to be within the range of 0.01–10 wt% of the hydrotalcite. If less than 0.01 wt% of ruthenium ions is adsorbed on hydrotalcites, a large amount of catalyst must be prepared, which is not desirable from an economic viewpoint. On the other hand, adsorbing more than 10 wt% of ruthenium ions is difficult to achieve because of the nature of hydrotalcites. This may be explained as follows. While hydrotalcites are represented by the rational formula noted a few paragraphs before, a hydrotalcite containing $Mg^{2+}$ as a divalent metal and $Al^{3+}$ as a trivalent metal may be represented as follows:

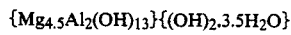

$$\{Mg_{4.5}Al_2(OH)_{13}\}\{(OH)_2.3.5H_2O\}$$

If, for example, ruthenium chloride is adsorbed on this hydrotalcite, it is speculated to have the following structure:

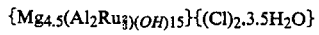

$$\{Mg_{4.5}(Al_2Ru_3)(OH)_{15}\}\{(Cl)_2.3.5H_2O\}$$

or

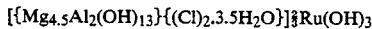

$$[\{Mg_{4.5}Al_2(OH)_{13}\}\{(Cl)_2.3.5H_2O\}]\cdot Ru(OH)_3$$

Therefore, ruthenium ions will theoretically be adsorbed on this specific type of hydrotalcite in an amount of 11%.

The catalyst of the present invention may have ions of metals other than ruthenium supported, subject to the condition that the objects of the invention will not be impaired.

The catalysts of the present invention is prepared by reducing the ruthenium ions adsorbed on a hydrotalcite. Upon reduction, ruthenium ions are considered to be converted to metallic ruthenium. This reduction treatment may be preceded by a heat treatment as required. By this heat treatment, anions that have been taken into the hydrotalcite together with ruthenium ions can be removed. The temperature for the heat treatment is preferably in the range of 300°–700° C.

Ruthenium ions adsorbed on the hydrotalcite may be reduced by any of the methods commonly employed for ruthenium reduction, including a method of reduction with hydrogen in vapor phase, as well as a method in which reduction is performed in liquid phase with either hydrogen or using an appropriate chemical reducing agent such as $NaBH_4$ or formalin. A preferred method is to perform reduction with hydrogen in either vapor or liquid phase.

With a view to enhancing the performance of metal-based catalysts, various attempts have so far been made to have metallic elements present on catalyst supports in a highly dispersed state. A method that has been proposed to achieve this end is to have metallic ions supported through adsorption by ion-exchange technology. Although being anion-exchange type, the catalyst of the present invention also has a metallic element supported by ion-exchange, so that the ions of the metal can be supported in a highly dispersed state. Furthermore, ruthenium which has been trapped in crystal lattices in the support hydrotalcite interacts so strongly with the constituent elements of the hydrotalcite that the preparation of a high-performance catalyst can be realized.

The catalyst of the present invention may be employed in various types of hydrogenation reaction and one of them is a process for producing cycloolefins, in particular, cyclohexenes, through partial hydrogenation of monocyclic aromatic hydrocarbons. This process is described hereinafter as an example of the use of the catalyst of the present invention.

The starting monocyclic aromatic hydrocarbon is selected from among benzene, toluene, xylenes and loweralkyl-benzenes. The presence of water is indispensable to the process of producing cyclohexenes using the catalyst of the present invention. Depending on the specific type of reaction involved, water may generally be present in an amount ranging from 0.1 to 50 times the weight of the starting monocyclic aromatic hydrocarbon. Water must be present in such an amount that under the reaction conditions employed it forms a two-component liquid phase, one being an aqueous phase and the other being an organic phase chiefly composed of the starting material and the reaction product. The effectiveness of water is reduced if it is present in an extremely small amount that provides a homogeneous phase under the reaction conditions employed. A similar result would occur if an excessively large amount of water were present. Using an excessive amount of water is also uneconomical since it becomes necessary to employ a larger reactor. Therefore, for practical purposes, water is desirably present in an amount ranging from 0.5 to 10 times the weight of the starting monocyclic aromatic hydrocarbon.

In the process described above, water may optionally be replaced by an aqueous alkaline solution. The aqueous alkaline solution to be used may have any pH that is not smaller than 7, and the alkali concentration may be increased up to 10% when an aqueous solution of sodium hydroxide is taken as an example.

Partial reduction of the monocyclic aromatic hydrocarbon is usually performed by a liquid-phase suspension method either continuously or batchwise. If desired, a fixed bed system may be employed. The reaction conditions vary with the state of the catalyst of the present invention used in the reaction and may be appropriately selected in accordance with the type of hydrotalcite used in the preparation of the catalyst or the quantity of ruthenium supported through adsorption on the hydrotalcite.

The hydrogen pressure for use in the reaction is generally in the range of 1–200 kgf/cm², preferably 10–100 kgf/cm². The reaction temperature is generally in the range of 50°–250° C., preferably 100°–200° C. The reaction time may be properly selected depending upon the selectivity and yield of the desired cyclohexene, and is normally in the range of from several minutes to several hours.

In accordance with a process for producing cycloolefins using the catalyst of the present invention, desired cycloolefins can be obtained in a high selectivity and yield that has not been attainable in the prior art. This shows that the catalyst of the present invention is industrially a very valuable substance.

Besides the process of producing cyclohexenes, the hydrogenation catalyst of the present invention is also applicable with advantage to other hydrogenation reaction such as the hydrogenation of carbonyl compounds and reduction of nitro compounds.

The following examples are provided for the purpose of further illustrating the present invention but are in no way to be taken as limiting.

EXAMPLE 1

A 300-ml separable flask equipped with a stirrer, a reflux condenser and an inlet through which to charge a solid powder was charged with 0.82 g of $RuCl_3:xH_2O$ (ca. 45 wt% Ru) and 200 ml of ion-exchanged water. As the contents of the flask were stirred at room temperature in a nitrogen stream, 4.8 g of a solid solution type of hydrotalcite composed of magnesium and aluminum ($Mg_{4.5}Al_2O_{7.5}$; "KW-2000" of Kyowa Kagaku K.K.) was thrown into the flask at a time. The stirring was continued for 12 hours at room temperature.

When the adsorption of ruthenium ions on the hydrotalcite came to an end, the brown color of ruthenium tri-chloride dissolved in water disappeared completely, indicating that all of the ruthenium ions available had been adsorbed. The hydrotalcite on which ruthenium ions were adsorbed was separated from the liquid phase with a centrifugal precipitator.

The solid cake obtained was dried under a nitrogen stream to obtain 8.35 g of a precursor of hydrotalcite catalyst having ruthenium ions supported thereon through adsorption. This precursor (8.35 g) was charged into a Hastelloy autoclave (inner capapcity, 500 ml) together with 200 ml of ion-exchange water. After replacing the inside of the autoclave with nitrogen, it was pressurized with hydrogen to 50 kgf/cm$^2$ and a reduction treatment was performed at 150° C. for 5 hours.

After separating the reaction mixture into solid and liquid phases with a centrifugal precipitator, the solid phase was vacuum-dried to form a cake weighing 6.62 g. A portion (2.0 g) of this cake was heat-treated at 500° C. for 2 hours under a nitrogen stream, thereby preparing 0.98 g of a hydrogenation catalyst. All of the steps following the reduction treatment were carried out in a nitrogen atmosphere in order to avoid contact with air.

The so prepared hydrogenation catalyst (0.2 g), ion-exchanged water (160 g) and benzene (40 g) were charged into a Hastelloy autoclave (inner capacity, 500 ml) and the temperature in the autoclave was started to rise after replacing its interior with nitrogen gas. When the temperature in the autoclave reached 150° C., hydrogen was pumped into the autoclave to build a pressure of 50 kgf/cm$^2$. As the hydrogenation reaction proceeded, the pressure in the autoclave would decrease, so additional hydrogen was supplied as appropriate to maintain the pressure of 50 kgf/cm$^2$. After 1-hr reaction, the autoclave was cooled and the contents were recovered. Gas chromatographic analysis of the oil phase as separated from the aqueous phase showed that the conversion of benzene was 16.3% to reduce cyclohexene in a yield of 7.6% (46.6% selectivity). The by-product was cyclohexane.

EXAMPLE 2

A 300-ml separable flask equipped with a stirrer, a reflux condenser and an inlet through which to charge a solid powder was charged with 2.5 g of Zn-containing hydrotalcite ($Mg_{3.5}ZnAl_2(OH)_{13}:CO_3:3.5H_2O$; "ZHT-1000" of Kyowa Kagaku K.K.) and 150 ml of ion-exchanged water. As the contents of the flask were stirred at room temperature, 100 g of a solution having 1 g of $RuCl_3 \cdot xH_2O$ (ca. 45 wt% Ru) dissolved in 200 ml of water was poured into the flask.

Following stirring for about 1 hour at room temperature, the contents were stirred for another 2 hours at 80° C. After the adsorption of ruthenium ions on the hydrotalcite had been completed, the reaction mixture was separated into a solid and a liquid phase with a centrifugal precipitator. The solid phase was dried under a nitrogen stream to obtain a precursor of hydrogenation catalyst in an amount of 2.57 g. Part (0.5 g) of this precursor was charged into a 100-ml Ti autolcave together with 50 ml of ion-exchanged water. After pressurizing the autoclave to 50 kgf/cm$^2$ with hydrogen, a reduction treatment was performed at 150° C. for 12 hours. After completion of the reduction step, the reaction mixture was separated into a solid and a liquid phase with a centrifugal precipitator.

The so obtained hydrogenation catalyst was transferred into a Ti autoclave (inner capacity, 500 ml), which was thereafter charged with 160 g of ion-exchanged water and 40 g of benzene. After replacing the atmosphere in the autoclave with nitrogen, the temperature in the autoclave was started to rise. When the autoclaving temperature reached 150° C., hydrogen was pumped in to commence the reaction. Following 20-min reaction at a pressure of 50 kgf/cm$^2$, the reaction mixture was recovered and separated into an oil phase and an aqueous phase. Analysis of the oil phase showed that the conversion of benzene was 57.7%, producing cyclohexene in a yield of 22.0% (38.2% selectivity).

EXAMPLE 3

Part (0.5 g) of the precursor of hydrogenation catalyst prepared in Example 2 which had ruthenium ions adsorbed on hydrotalcite was charged into a 100-ml Ti autoclave together with 50 ml of a 1% aqueous solution of sodium hydroxide. After pressurizing the autoclave to 50 kgf/cm$^2$ with hydrogen, a reduction treatment was performed at 150° C. for 12 hours. After completion of the reduction step, the reaction mixture was separated into a solid and a liquid phase with a centrifugal precipitator.

The hydrogenation catalyst thus obtained was transferred into a Ti autoclave (inner capacity, 500 ml), which was subsequently charged with 160 g of a 1% aqueous solution of sodium hydroxide and 40 g of benzene. After replacing the atmosphere in the autoclave with nitrogen, the temperature in the autoclave was started to rise. When the autoclaving temperature reached 150° C., hydrogen was pumped in to commence the reaction. Following 40-min reaction at a pressure of 50 kgf/cm$^2$, the reaction mixture was recovered and separated into an oil phase and an aqueous phase. Analysis of the oil phase showed that the conversion of benzene was 45.9%, producing cyclohexene in a yield of 26.2% (57.1% selectivity).

EXAMPLE 4

Part (0.5 g) of the precursor of hydrogenation catalyst prepared in Example 2, which had ruthenium ions adsorbed on hydrotalcite was heated in a quartz tube at 500° C. for 2 hours under a nitrogen stream. The heat-treated precursor was charged into a 100-ml Ti autoclave together with 50 ml of ion-exchanged water. After pressurizing the autoclave to 50 kgf/cm$^2$ with hydrogen, a reduction treatment was performed at 150° C. for 12 hours. After completion of the reduction step, the reaction mixture was separated into a solid and a liquid phase by means of a centrifugal precipitator.

The hydrogenation catalyst obtained was transferred into a Ti autoclave (inner capacity, 500 ml), which was subsequently charged with 160 g of ion-exchanged water and 40 g of benzene. After replacing the atmosphere in the autoclave with nitrogen, the temperature in the autoclave was started to rise. When the autoclaving temperature reached 150° C., hydrogen was pumped in to commence the reaction. Following 50-min reaction at a pressure of 50 kgf/cm², the reaction mixture was recovered and separated into an oil phase and an aqueous phase. Analysis of the oil phase showed that 43.5% of benzene had been converted, producing cyclohexene in a yield of 18.4% (42.4% selectivity).

The hydrogenation catalyst of the present invention has ruthenium supported on a hydrotalcite and/or a compound that can be converted to a hydrotalcite structure by hydration. In this catalyst, ruthenium ions are present on the support in a highly dispersed state and ruthenium which has been trapped in crystal lattices in the support hydrotalcite interacts so strongly with the constituent elements of the hydrotalcite that high performance is imparted to the catalyst. One application of this catalyst is in the production of cycloolefins from monocyclic aromatic hydrocarbons and by using this catalyst, cycloolefins can be produced in high selectivity and yield that has been unattainable in the prior art.

What is claimed is:

1. A hydrogenation catalyst for producing cycloolefins from monocyclic aromatic hydrocarbons, wherein said catalyst is prepared by adsorbing ruthenium ions on a hydrotalcite support or a compound capable of conversion to a hyrotalcite structure by hydration, and then reducing the adsorbed ruthenium ions.

2. The hydrogenation catalyst of claim 1 wherein the hydrotalcite is a natural hydrotalcite, a synthetic hydrotalcite of a mixture of both.

3. The hydrogenation catalyst of claim 1 wherein the hydrotalcite support material has the formula:

$$\{M_{1-x}^{2+}M_x^{3+}(OH)_2\}^{x+}\{A_{x/n}^{n-}\cdot mH_2O\}^{x-}$$

or $$\{M_{1-x}^{2+}M_x^{3+}O_{1+x/2}\}$$

in which $M^{2+}$ is a divalent metal ion selected from $Mg^{2+}$, $Mn^{2+}$, $Fe^{2+}$, $Co^{2+}$, $Ni^{2+}$, $Cu^{2+}$, $Zn^{2+}$ or a mixture thereof;

$M^{3+}$ is a trivalent metal selected from $Al^{3+}$, $Fe^{3+}$, $Cr^{3+}$, $Co^{3+}$, $In^{3+}$ or mixtures thereof;

$A^{n-}$ is an n-valent anion selected from $OH^-$, $F^-Cl^-$, $Br^-$, $NO_3^-$, $CO_3^{2-}$, $SO_4^{2-}$, $CH_3COO^-$, oxalate ion, salicylate ion, or a mixture of these ions wherein n is 1 or 2; and $O < X \leq 0.33$.

4. The hydrogenation catalyst of claim 3, having the formula:

$$\{Mg_{4.5}Al_2(OH)_{13}\}\{(OH)_2\cdot 3.5H_2O\}.$$

5. The hydrogenation catalyst of claim 1, wherein the ruthenium supported on the hydrotalcite represents from about 0.01 to about 10% by weight of the hydrotalcite.

6. A process for preparing a hydrogenation catalyst for producing cycloolefins from monocyclic aromatic hydrocarbons, comprising the steps of:
   (a) adsorbing ruthenium ions on a hydrotalcite structure by dehydration, and thereafter
   (b) reducing the adsorbed ruthenium ions in the presence of a reducing agent to metallic ruthenium.

7. The process of claim 6, wherein the ruthenium ions supported on the hydrotalcite are from about 0.01 to about 10% by weight of the weight of the hydrotalcite.

* * * * *